US00PP26698P3

(12) United States Plant Patent
Jansen

(10) Patent No.: US PP26,698 P3
(45) Date of Patent: May 3, 2016

(54) ***PENSTEMON* PLANT NAMED 'CHA CHA PURPLE'**

(50) Latin Name: ***Penstemon* hybrid**
Varietal Denomination: Cha Cha Purple

(71) Applicant: Terra Nova Nurseries, Inc., Canby, OR (US)

(72) Inventor: Robert D. Jansen, Naalehu, HI (US)

(73) Assignee: Terra Nova, Inc., Canby, OR (US)

( * ) Notice: Subject to any disclaimer, the term of this patent is extended or adjusted under 35 U.S.C. 154(b) by 139 days.

(21) Appl. No.: 14/120,092

(22) Filed: Apr. 24, 2014

(65) Prior Publication Data

US 2015/0313074 P1 Oct. 29, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Keith Robinson
(74) *Attorney, Agent, or Firm* — Klarquist Sparkman, LLP

(57) ABSTRACT

A new and distinct cultivar of *Penstemon* plant characterized by medium size red purple flowers in dense clusters, long bloom time, a compact, upright, well branched habit, with multiple crown from the base, clean-looking, deep green, attractive foliage, and excellent vigor.

1 Drawing Sheet

Botanical denomination: *Penstemon* hybrid.
Variety designation: 'Cha Cha Purple'.

BACKGROUND OF THE INVENTION

The present invention relates to a new and distinct cultivar of *Penstemon*, given the name, 'Cha Cha Purple'. *Penstemon* is in the family Scrophulariaceae. This plant originated in a controlled breeding plan to create a compact, upright, medium size, multiflowered series. The exact parents are unknown, unnamed proprietary plants. This cultivar was selected for its compact growing habit, medium size flowers in dense clusters, long flowering time, vigor, and clean attractive look. It is an ideal plant for a sunny border in full sun.

Compared to *Penstemon* 'Grape Taffy', U.S. Plant Pat. No. 22,567, the new cultivar has smaller more numerous flowers with no white eye, and smaller, narrower leaves.

Compared to *Penstemon* 'Boysenberry Taffy', U.S. Plant Patent No. applied for, the new cultivar smaller more numerous flowers that are more red purple than purple, and smaller, narrower leaves.

Compared to *Penstemon* 'Burgundy', an unpatented plant, the new cultivar is hardier with smaller more numerous flowers, and smaller, narrower leaves.

*Penstemon* 'Cha Cha Purple' is uniquely distinguished by its:

1. medium size red purple flowers in dense clusters,
2. long bloom time,
3. compact, upright, well branched habit, with multiple crown from the base,
4. clean-looking, deep green, attractive foliage, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the new cultivar as a 10 month old in the trial field in full bloom in mid July in Canby, Oreg.

FIG. 2 shows the habit of the same 10 month-old plant.

DETAILED PLANT DESCRIPTION

The following is a detailed description of the new *Penstemon* cultivar based on observations of 18 month-old specimens grown outside in five gallon containers in full sun in Canby, Oreg. in October. The color descriptions are all based on *The Royal Horticultural Society Colour Chart*, 5$^{th}$ edition, 2007.

Plant:

*Type*.—Herbaceous perennial.
*Form*.—Upright, branching.
*Cold hardiness*.—USDA Zone 7-10.
*Size*.—Grows to 50 cm wide and 54 cm high.
*Vigor*.—Excellent.
*Stem number*.—About 12 main stems from the crown.
*Stem strength*.—Strong.
*Stem*.—Upright, grows to 49 cm long and 1 cm wide (at the base), glabrous at base to glandular pubescent toward peduncle, internodes grow to 3.5 cm long, Yellow Green 146C where shaded and tinted Red Purple 59B where in sun.
*Roots and rooting*.—Fibrous root system, White 155C, roots easily from stem cuttings in 10 to 14 days.

Leaf:

*Type*.—Simple.
*Arrangement*.—Opposite.

*Shape*.—Lanceolate.
*Venation*.—Pinnate, main vein on top and bottom side Yellow Green 146C.
*Margins*.—Serrulate.
*Apex*.—Acuminate.
*Base*.—Attenuate.
*Petiole*.—None, sessile.
*Blade size*.—Grows to 9 cm long and 1.4 cm wide.
*Surface texture*.—Glabrous on both sides.
*Leaf color*.—Topside Green 137A, bottom side closest to Yellow Green 146A.

Inflorescence:
*Type*.—Terminal, many flowered, dense thyrse.
*Number of flowers per inflorescence*.—25 to 33.
*Size of inflorescence*.—Grows to 15 cm long and 8 cm wide.
*Peduncle*.—Strong, upright, grows to 2 cm long and 2.5 mm wide, pubescent, Yellow Green 146C where shaded and tinted Greyed Purple 187A where in sun.
*Pedicel*.—Medium strength, grows semi-upright to 1 cm long and 1 mm wide, pubescent, Yellow Green 146C in shade and lightly tinted Greyed Purple 187B where in sun.
*Bloom period*.—Mid June to frost in October in Canby, Oreg. if spent flowers are removed.

Flower bud:
*Size*.—3.5 cm long and 12 mm wide.
*Description*.—Closed tubular, bulging, flattened ventrically, pubescent.
*Color*.—Purple 77A with tip 83B.

Flower:
*Type*.—Zygomorphic, perfect.
*Shape*.—Tubular, bilabiate.
*Size*.—Grows to 3.8 cm long and 3.2 cm wide.
*Corolla description*.—Grows to 3.8 cm long and 3.2 cm wide; tube is bulbous in the calyx for 6 mm long and 5 mm wide, narrowing then widening for 21 mm and flaring to 32 mm wide, 5 lobes, the two smaller top lobes flare back (each 8 mm wide and to 10 mm deep) and two larger lateral lobes curl back (16 mm wide and 15 mm deep), and the lower lobe flares curls back slightly (13 mm wide and 13 mm deep), lobes overlap, lobe margins entire to slightly jagged, tips obtuse; outside glandular pubescent, inside sparsely pubescent; outside color Purple 77A, inside color lobes Purple 77A with edges N77A and base of lower 3 lobes N77A changing to bee tracks in tube N77A, inside tube color 76D.
*Calyx description*.—10 mm deep and 9 mm wide, 5 overlapping lobes cut to the base, each lobe broadly ovate in shape, 10 mm deep and 6 mm wide, margins variable (entire, notched and trident), tip acuminate, base cuneate, outside Yellow Green 146C tinted Greyed Purple 187A where in sun and on margins, inside Yellow Green 146C, glabrous inside and glandular pubescent outside.
*Pistil description*.—1, 35 mm long, ovary 6 mm long and 2 mm wide, Yellow Green 146D; style 29 mm long and less than 1 mm wide, style Purple N78A lighting toward tip, stigma shape conical, White NN155C.
*Stamen description*.—5, one sterile without an anther, held within the corolla 29 mm long, filaments 23 to 30 mm long and White NN155C, anthers oval, 2 mm long, Greyed Purple N186A, pollen amount moderate, White NN155C.
*Fragrance*.—None.
*Lastingness*.—A flower lasts 5 to 6 days.

Fruit:
*Type*.—Capsule.
*Fertility*.—Good.
*Size*.—7 mm deep and 1 mm wide.
*Texture*.—Pubescent.
*Color*.—Brown N199C.

Seed:
*Shape*.—Irregular.
*Size*.—2 mm long.
*Texture*.—Glabrous.
*Color*.—Brown 200A.

Pests and diseases: The new cultivar is typical to the genus. No problems have been found in Canby, Oreg.

I claim:

1. A new and distinct cultivar of *Penstemon* plant substantially as shown and described.

* * * * *

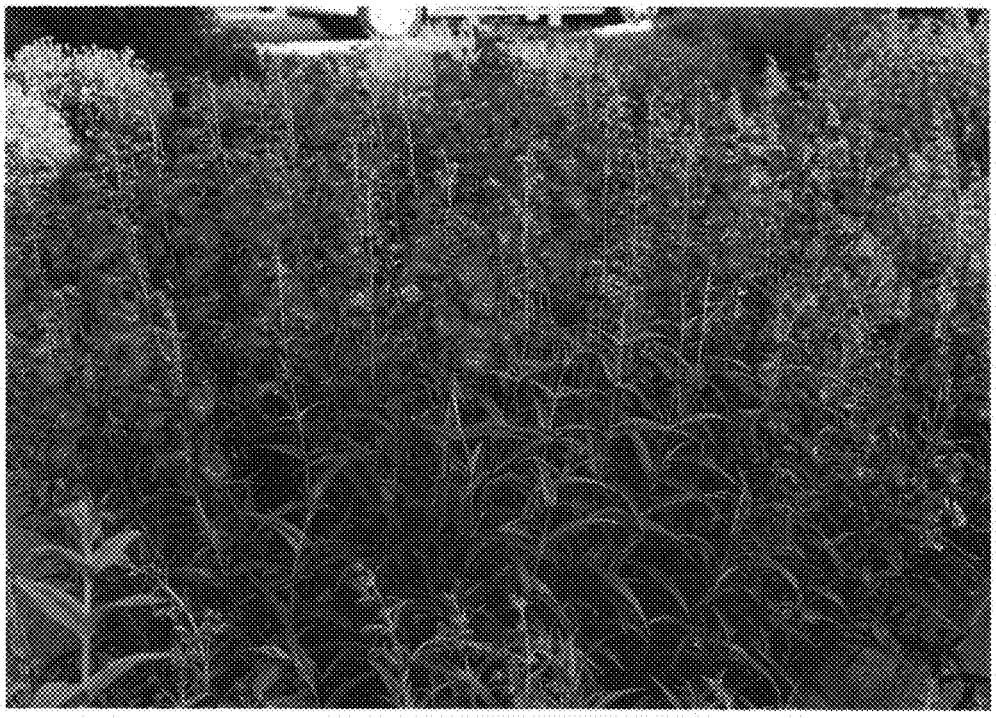

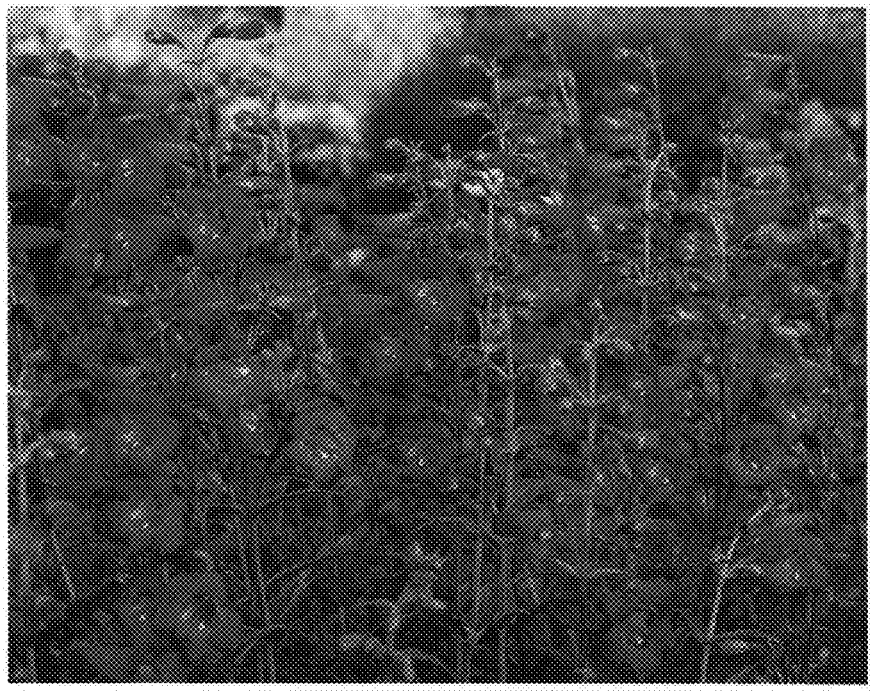
FIG. 1 above, FIG. 2 below